US00PP18128P2

(12) United States Plant Patent
Kerley et al.

(10) Patent No.: US PP18,128 P2
(45) Date of Patent: Oct. 16, 2007

(54) ***PETUNIA* PLANT NAMED 'KERSAMFAN'**

(50) Latin Name: *Petunia×hybrida*
Varietal Denomination: Kersamfan

(76) Inventors: David W. Kerley, Bethany, 49 Station Road, Over, Cambridge CB4 5NJ (GB); Priscilla G. Kerley, Bethany, 49 Station Road, Over, Cambridge CB4 5NJ (GB)

( * ) Notice: Subject to any disclaimer, the term of this patent is extended or adjusted under 35 U.S.C. 154(b) by 0 days.

(21) Appl. No.: 11/298,795

(22) Filed: Dec. 9, 2005

(51) Int. Cl.
*A01H 5/00* (2006.01)

(52) U.S. Cl. ..... Plt./356
(58) Field of Classification Search ..... Plt./356
See application file for complete search history.

(56) References Cited

PUBLICATIONS

Internet website http://web.archive.org/web/20041014050442/http://www.kerley.co.uk/pet_fan_salmon.htm (2 pages total), dated Oct. 14, 2004.*

UPOV–ROM GTITM, Plant Variety Database, 2006/03, GTI Jouve Retrieval Software, citation for 'Kersamfan' (1 page total).*

* cited by examiner

*Primary Examiner*—Kent Bell
*Assistant Examiner*—S. B. McCormick-Ewoldt
(74) *Attorney, Agent, or Firm*—Audrey Charles

(57) ABSTRACT

A new and distinct cultivar of *Petunia* plant named 'Kersamfan' characterized by its salmon-colored flowers with deep salmon-colored veins, large single-type flowers, excellent branching, and semi-trailing growth habit.

1 Drawing Sheet

Latin name of genus and species of plant claimed: *Petunia×hybrida.*
Variety denomination: 'Kersamfan'.

BACKGROUND OF THE INVENTION

The present invention relates to a new and distinct cultivar of *Petunia* plant botanically known as *Petunia×hybrida* and hereinafter referred to by the cultivar name 'Kersamfan'.

The new cultivar originated in a controlled breeding program in Cambridge, United Kingdom during August 2001. The objective of the breeding program was the development of *Petunia* cultivars having single-type flowers with unique flower colors and vigorous, mounded, and trailing growth habit.

The female (seed) parent of the new cultivar was the proprietary *Petunia×hybrida* breeding selection designated 01-120-1, not patented, characterized by its single-type, pink flushed white-colored flowers and upright growth habit. The male (pollen) parent of the new cultivar was 'Kercan', U.S. Plant Pat. No. 13,787, characterized by its double-type, pink-colored flowers with deep pink-colored veins and semi-trailing growth habit. The new *Petunia* was discovered and selected by the inventor as a single flowering plant within the progeny of the above stated cross-pollination during May 2002 in a controlled environment at Cambridge, United Kingdom.

Asexual reproduction of the new cultivar by terminal stem cuttings since May 2002 at Cambridge, United Kingdom and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Kersamfan' as a new and distinct cultivar of *Petunia* plant:

1. Salmon-colored flowers with deep salmon-colored veins;
2. Large single-type flowers;
3. Excellent branching; and
4. Semi-trailing growth habit.

Plants of the new cultivar differ from plants of the female parent primarily in flower color and growth habit and from plants of the male parent primarily in flower color and flower type.

Of the many commercially available *Petunia* cultivars known to the inventor, the most similar in comparison to the new cultivar is 'Kercofan', unpatented. However, in side by side comparisons, plants of the new cultivar differ from plants of 'Kercofan' in the following characteristics:

1. Plants of the new cultivar have a flower color different from plants of 'Kercofan'; and
2. Plants of the new cultivar have more prominent flower petal venation than plants of 'Kercofan'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Kersamfan'. The plants were grown 3 plants per pot in 20 cm pots for 10 weeks in a greenhouse at Cambridge, United Kingdom.

DETAILED BOTANICAL DESCRIPTION

Figure 1:
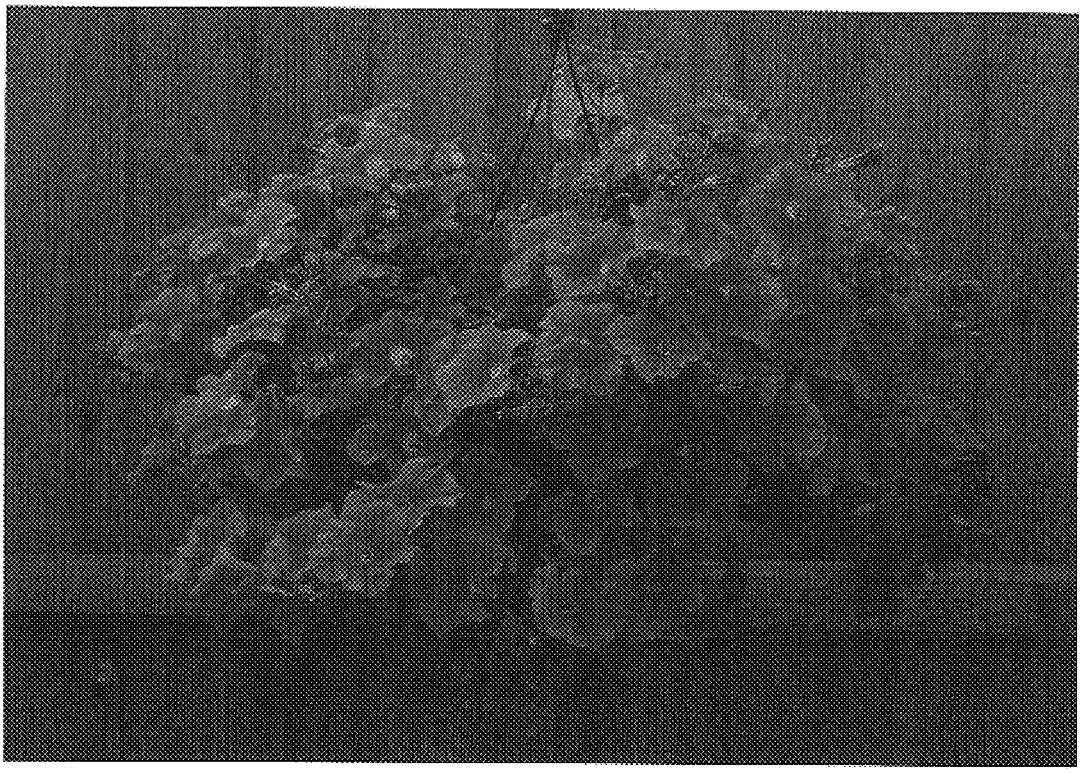
FIG. 1 illustrates a side view of the overall growth and flowering habit of 'Kersamfan'.
Figure 2:
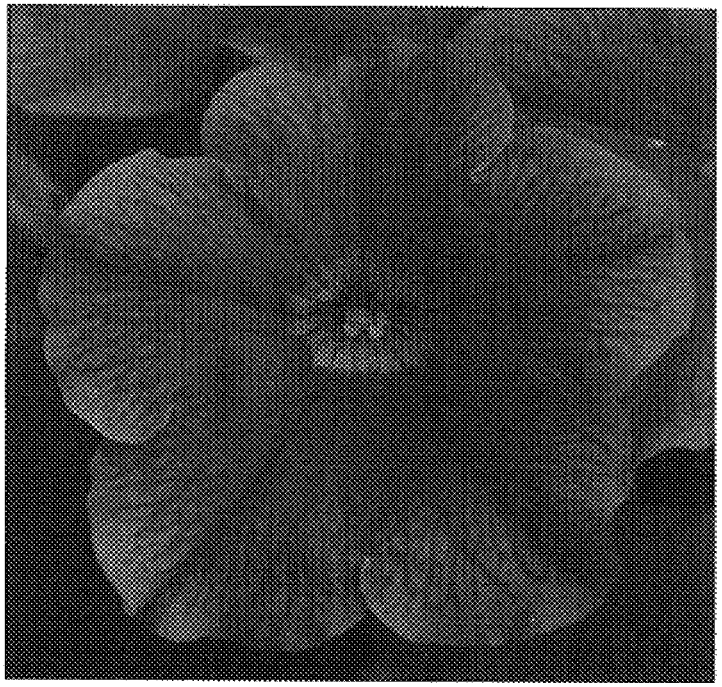
FIG. 2 illustrates a close-up view of an individual flower of 'Kersamfan'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The Royal Horticultural Society Colour Chart of The Royal Horticultural Society, London, England, 1995 edition, except where general color terms of ordinary significance are used. The color values were determined on Jun. 30, 2005 between 3:00 p.m. and 4:00 p.m. under 50% shade light conditions, in Cambridge, United Kingdom.

The following descriptions and measurements describe plants produced from cuttings taken from stock plants and grown in a glass-covered greenhouse under conditions comparable to those used in commercial practice. The plants were grown at Cambridge, United Kingdom 3 plants in each 20 cm pot for 10 weeks utilizing a soilless growth medium. Greenhouse temperatures were maintained at approximately 64° F. to 82° F. (18° C. to 28° C.) during the day and approximately 57° F. to 68° F. (14° C. to 20° C.) during the night. Greenhouse light levels of an average of 4,645 footcandles were maintained during the day.

Botanical classification: *Petunia×hybrida* cultivar Kersamfan.

Parentage:

*Female parent.*—Proprietary *Petunia×hybrida* breeding selection designated 01-120-1, not patented.

*Male parent.*—'Kercan', U.S. Plant Pat. No. 13,787.

Propagation:

*Type cutting.*—Terminal stem.

*Time to initiate roots.*—Approximately 10 to 14 days.

*Time to produce a rooted cutting.*—Approximately 30 to 45 days.

*Root description.*—Fine, fibrous.

*Rooting length.*—Freely branching.

Plant description:

*Crop time.*—Approximately 6 to 8 weeks from a rooted cutting.

*Growth habit and general appearance.*—Semi-trailing.

*Size.*—Height from soil level to top of plant plane: Approximately 20 cm. Height from bottom of trailing stem to top of plant: Approximately 55 cm. Width: Approximately 60 cm.

*Branching habit.*—Freely basal branching, pinching improves branching. Approximately 5 main branches per plant with lateral branches potentially forming at every node.

*Branch.*—Strength: Moderate to strong. Length: Approximately 56.0 cm. Diameter: Approximately 5.0 mm. Texture: Pubescent. Color of mature stem: 144A. Internode length at center of branch: Approximately 5.3 cm.

*Foliage.*—Number of leaves per main branch: Approximately 14. Form: Simple. Arrangement on flowering stem: Opposite. Aspect: Obtuse angle to stem. Shape: Elliptic. Margin: Entire, slightly undulating. Apex: Acute. Base: Acute. Venation pattern: Pinnate. Length of mature leaf: Approximately 4.1 cm. Width of mature leaf: Approximately 2.6 cm. Texture of upper surfaces: Pubescent, slightly coarse. Texture of lower surfaces: Sparsely pubescent. Color of upper surface of young foliage: Between 137B and 137C. Color of lower surface of young foliage: 147B. Color of upper surface of mature foliage: 137A with venation of 144A. Color of lower surface of mature foliage: 147B with venation of 144B. Petiole length: Approximately 4.7 mm. Petiole diameter: Approximately 2.8 mm. Petiole texture: Pubescent. Petiole color of upper surface: Between 144A and 144B. Petiole color of lower surface: 144A.

Flowering description:

*Flowering habit.*—'Kersamfan' is freely flowering under outdoor growing conditions with substantially continuous blooming from spring through autumn.

*Time to first flower.*—Approximately 8.5 weeks after sticking of unrooted cutting.

*Lastingness of individual bloom.*—Approximately 10 days.

Flower description:

*Type.*—Simple, salverform and self-cleaning. Aspect: Outward. Fragrance: None. Quantity per lateral stem at ten weeks: Approximately 17. Quantity of flowers and buds per plant at ten weeks: Approximately 120.

*Bud rate of opening.*—Generally takes 1 to 2 days for bud to progress from first color to fully open flower.

*Bud just before opening.*—Quantity per lateral stem at ten weeks: Approximately 7.5. Shape: Oblong. Length: Approximately 3.3 cm. Diameter: Approximately 7.2 mm. Texture: Densely pubescent. Color: 145A.

*Corolla.*—Diameter: Approximately 7.3 cm. Depth/Height: Approximately 2.4 cm.

*Petals.*—Quantity: 5 fused to form a tube. Shape: Obovate. Apex: Obtuse, undulation causes it to appear acute. Margin: Entire, undulating. Appearance: Prominently veined. Texture of upper surface: Glabrous. Texture of lower surface: Sparsely pubescent. Texture of throat: Glabrous. Length of petal from throat: Approximately 3.4 cm. Petal width: Approximately 2.8 cm. Color of upper surface when opening: 61D with venation between 53A and 53B. Color of upper surface when fully open: 61D with venation between 53A and 53B that fades to 54B. Color of lower surface when opening and fully open: 63C with venation of 144A. Color of throat: 1D with venation of 183A.

*Corolla tube.*—Length: Approximately 2.3 cm. Diameter at distal end: Approximately 1.6 cm. Diameter at proximal end: Approximately 4.3 mm. Texture of outer surface: Pubescent, somewhat coarse. Texture of inner surface: Glabrous. Color of outer surface: 144D with venation of 145A. Color of inner surface: 1D with venation of 183A.

*Peduncle.*—Strength: Strong. Aspect: Acute angle to stem. Length: Approximately 2.1 cm. Diameter: Approximately 2.0 mm. Texture: Pubescent. Color: 144A.

*Sepals.*—Quantity per flower: 5 fused at base. Shape: Narrow, oblong. Margin: Entire, slightly undulating. Apex: Obtuse. Base: Acute. Sepal length: Approximately 2.0 cm. Sepal width: Approximately 5.5 mm. Texture of upper and lower surfaces: Pubescent. Color of upper surface: 147A. Color of lower surface: 146A.

*Reproductive organs.*—Androecium: Stamen quantity: 5 fused at base to inside of corolla tube. Anther shape: Bilobed. Anther length: Approximately 3.0 mm. Anther color: 4D. Pollen amount: Abundant. Pollen color: 8C. Gynoecium: Pistil quantity: 1 per flower. Pistil length: Approximately 1.8 cm. Stigma shape: Funnel. Stigma color: Between 144A and 144D. Style length: Approximately 1.5 cm. Style color: 145B. Ovary color: 145A.

*Fruit.*—Classification: Dry capsule. Shape: Conical. Diameter: Approximately 5.1 mm. Texture: Smooth. Color of immature fruit: 146D at base transitioning to 146A at tip. Color of mature fruit: 199B at base transitioning to 199A at tip.

*Seed.*—Quantity: 60 to 200 per capsule. Diameter: Approximately 0.5 mm. Color: 200A to 200C.

Disease and pest resistance: Resistance to pathogens and pests common to *Petunia* has not been observed.

What is claimed is:

1. A new and distinct cultivar of *Petunia* plant named 'Kersamfan', substantially as herein shown and described.

* * * * *